United States Patent
Barty (10) Patent No.: US 9,983,151 B2
(45) Date of Patent: May 29, 2018

(54) ULTRALOW-DOSE, FEEDBACK IMAGING WITH LASER-COMPTON X-RAY AND LASER-COMPTON GAMMA RAY SOURCES

(71) Applicant: LAWRENCE LIVERMORE NATIONAL SECURITY, LLC, Livermore, CA (US)

(72) Inventor: Christopher P. J. Barty, Hayward, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days. days.

(21) Appl. No.: 15/320,047

(22) PCT Filed: May 7, 2015

(86) PCT No.: PCT/US2015/029742
§ 371 (c)(1),
(2) Date: Dec. 19, 2016

(87) PCT Pub. No.: WO2015/171927
PCT Pub. Date: Nov. 12, 2015

(65) Prior Publication Data
US 2017/0153187 A1    Jun. 1, 2017

Related U.S. Application Data

(63) Continuation of application No. 14/274,348, filed on May 9, 2014.
(Continued)

(51) Int. Cl.
*H05G 2/00*     (2006.01)
*G01N 23/04*    (2018.01)
*G01N 9/24*     (2006.01)

(52) U.S. Cl.
CPC ............... *G01N 23/04* (2013.01); *G01N 9/24* (2013.01); *H05G 2/00* (2013.01)

(58) Field of Classification Search
CPC ....................................................... H05G 2/00
See application file for complete search history.

(56) References Cited

U.S. PATENT DOCUMENTS 3,780,294 A    12/1973    Sowerby
3,854,049 A    12/1974    Mistretta et al.
(Continued)

FOREIGN PATENT DOCUMENTS

EP    06006783         6/1994
JP    2012173076 A     9/2012
(Continued)

OTHER PUBLICATIONS

International Search Report and Written Opinion of the ISA for PCT/US2015/029742, ISA/KR, Daejeon, mailed Aug. 19, 2015.
(Continued)

*Primary Examiner* — Dani Fox
(74) *Attorney, Agent, or Firm* — John P. Wooldridge (57) ABSTRACT

Ultralow-dose, x-ray or gamma-ray imaging is based on fast, electronic control of the output of a laser-Compton x-ray or gamma-ray source (LCXS or LCGS). X-ray or gamma-ray shadowgraphs are constructed one (or a few) pixel(s) at a time by monitoring the LCXS or LCGS beam energy required at each pixel of the object to achieve a threshold level of detectability at the detector. An example provides that once the threshold for detection is reached, an electronic or optical signal is sent to the LCXS/LCGS that enables a fast optical switch that diverts, either in space or time the laser pulses used to create Compton photons. In this way, one prevents the object from being exposed to any further Compton x-rays or gamma-rays until either the laser-Comp-
(Continued)

ton beam or the object are moved so that a new pixel location may be illumination.

34 Claims, 3 Drawing Sheets

Related U.S. Application Data (60) Provisional application No. 61/990,637, filed on May 8, 2014.

(56)  References Cited

U.S. PATENT DOCUMENTS

| | | | |
|---|---|---|---|
| 4,598,415 | A | 7/1986 | Luccio et al. |
| 5,040,200 | A | 8/1991 | Ettinger et al. |
| 5,115,459 | A | 5/1992 | Bertozzi |
| 5,247,562 | A | 9/1993 | Steinbach |
| 5,293,414 | A | 3/1994 | Ettinger et al. |
| 5,323,004 | A | 6/1994 | Ettinger et al. |
| 5,353,291 | A | 10/1994 | Sprangle et al. |
| 5,420,905 | A | 5/1995 | Bertozzi |
| 5,847,863 | A | 12/1998 | Galvanauskas et al. |
| 6,035,015 | A | 3/2000 | Ruth et al. |
| 6,442,233 | B1 | 8/2002 | Grodzins et al. |
| 6,661,818 | B1 | 12/2003 | Feldman et al. |
| 6,684,010 | B1 | 1/2004 | Morris, Jr. et al. |
| 6,687,333 | B2 | 2/2004 | Carroll et al. |
| 7,060,983 | B2 | 6/2006 | Turner |
| 7,120,226 | B2 | 10/2006 | Ledoux et al. |
| 7,277,526 | B2 | 10/2007 | Rifkin et al. |
| 7,391,850 | B2 | 6/2008 | Kaertner et al. |
| 7,564,241 | B2 | 7/2009 | Barty et al. |
| 7,596,208 | B2 | 9/2009 | Rifkin et al. |
| 7,693,262 | B2 | 4/2010 | Bertozzi et al. |
| 8,369,480 | B2 | 2/2013 | Barty |
| 8,487,285 | B2 | 7/2013 | Matsumoto et al. |
| 8,693,637 | B2 | 4/2014 | Lee et al. |
| 8,934,608 | B2 | 1/2015 | Barty |
| 9,706,631 | B2 | 7/2017 | Barty |
| 2002/0057760 | A1 | 5/2002 | Carroll et al. |
| 2004/0109532 | A1 | 6/2004 | Ford et al. |
| 2004/0159803 | A1 | 8/2004 | Akselrod et al. |
| 2004/0240037 | A1 | 12/2004 | Harter |
| 2005/0179911 | A1 | 8/2005 | Boomgarden et al. |
| 2005/0226278 | A1 | 10/2005 | Gu et al. |
| 2006/0166144 | A1 | 7/2006 | Te Kolste et al. |
| 2006/0188060 | A1 | 8/2006 | Bertozzi et al. |
| 2006/0193433 | A1 | 8/2006 | Ledoux et al. |
| 2006/0249685 | A1 | 11/2006 | Tanaka |
| 2006/0251217 | A1 | 11/2006 | Kaertner et al. |
| 2007/0177640 | A1 | 8/2007 | Liu |
| 2007/0263767 | A1 | 11/2007 | Brondo |
| 2009/0045355 | A1 | 2/2009 | Desbrandes |
| 2009/0147920 | A1 | 6/2009 | Barty et al. |
| 2011/0007760 | A1 | 1/2011 | Clowes et al. |
| 2011/0064200 | A1* | 3/2011 | Bertozzi .......... G01N 23/20066 378/88 |
| 2012/0288065 | A1 | 11/2012 | Graves et al. |
| 2014/0287140 | A1 | 9/2014 | Perin |
| 2014/0328457 | A1 | 11/2014 | Stutman et al. |

FOREIGN PATENT DOCUMENTS

| | | |
|---|---|---|
| WO | 2005081017 A1 | 9/2005 |
| WO | 2007038527 A1 | 4/2007 |
| WO | 2009086503 A1 | 7/2009 |
| WO | 2009097052 A1 | 8/2009 |
| WO | 2011071563 A1 | 6/2011 |

OTHER PUBLICATIONS

First Office Action and Search Report for Chinese Patent Application 201580036385.x dated Jul. 26, 2017, 12 pp.
Boucher, S., et al., "Inverse compton scattering gamma ray source", Nuclear Instruments and Methods in Physics Research, A 608, 2008, pp. S54-S56.
Gibson, D.J., et al., "Design and operation of a tunable MeV-level Compton-scattering-based x-ray source", The American Physical Society, Physical Review and Special Topics—Accelerators and Beams, 13, 2010, 12 pp.
Hagmann, C.A., et al., "Transmission-based detection of nuclides with nuclear resonance fluorescence using a quasimonoenergetic photon source", J. Appl. Phys., vol. 106, 2009, pp. 1-7.
Jovanovic, I, et al., "High-power picosecond pulse recirculation for inverse compton scattering", Nuclear Physics B, 184, 2008, pp. 289-294.
Shverdin, M.Y., et al., "High-power picosecond laser pulse recirculation", Optics Letters, vol. 35, No. 13, 2010, pp. 2224-2226.
Zamfir, N.V., et al., "Extreme light infrastructure: nuclear physics", Proc. of SPIE, vol. 8080, pp. 1-8.
International Search Report and Written Opinion for PCT/US12/054872 related to U.S. Appl. No. 14/343,706, 9 pp.
International Search Report and Written Opinion for PCT/US12/047483 related to U.S. Appl. No. 13/552,610, 9 pp.
First Examination Report for corresponding New Zealand Application No. 727182, dated May 11, 2017, 7 pp.

\* cited by examiner

ULTRALOW-DOSE, FEEDBACK IMAGING WITH LASER-COMPTON X-RAY AND LASER-COMPTON GAMMA RAY SOURCES

CROSS-REFERENCE TO RELATED APPLICATIONS

This application claims the benefit of U.S. Provisional application 61/990,637, titled "Ultralow-Dose, Feedback Imaging System and Method Using Laser-Compton X-Ray or Gamma-Ray Source", filed May 8, 2014 and incorporated herein by reference. This is a continuation-in-part of U.S. patent application Ser. No. 14/274,348 titled "Modulated Method for Efficient, Narrow-Bandwidth, Laser Compton X-Ray and Gamma-Ray Sources," filed May 9, 2014, incorporated herein by reference. U.S. patent application Ser. No. 14/274,348 claims the benefit of U.S. Provisional Patent Application No. 61/821,813 titled "Modulated, Long-Pulse Method for Efficient, Narrow-Bandwidth, Laser Compton X-Ray and Gamma-Ray Sources," filed May 10, 2013, incorporated herein by reference. U.S. patent application Ser. No. 14/274,348 claims the benefit of U.S. Provisional application 61/990,637, titled "Ultralow-Dose, Feedback Imaging System and Method Using Laser-Compton X-Ray or Gamma-Ray Source", filed May 8, 2014 and incorporated herein by reference. U.S. patent application Ser. No. 14/274,348 claims the benefit of U.S. Provisional application 61/990,642, titled "Two-Color Radiography System and Method with Laser-Compton X-Ray Sources", filed on May 8, 2014 and incorporated herein by reference.

STATEMENT REGARDING FEDERALLY SPONSORED RESEARCH OR DEVELOPMENT

The United States Government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND OF THE INVENTION

Field of the Invention

The present invention relates to x-ray and gamma-ray imaging, and more specifically, it relates to techniques for lowering the dose required in such imaging techniques.

Description of Related Art

In conventional 2-D x-ray/gamma-ray imaging the patient or object is illuminated with a wide field of x-rays or gamma-rays and the transmitted signal is recorded on a 2D film or array of detectors. Variations of density within the object cause variations in transmission for the penetrating radiation and these variations appear as shadows on film or a detector array. The dynamic range of this imaging technique is determined by the response function of the detector system. In addition all parts of the object see the same input flux (photons per unit area) and the total dose impinging upon the object is set by the area of the object and the flux required to penetrate the most dense region of the object, i.e., the flux required to resolve the structures of interest within the object. In this imaging modality, the entire object sees a high dose.

Suggestions for pixel by pixel feedback imaging have been made previously in which a rotating anode, bremsstrahlung source is used in place of a laser-Compton source. In this case, upon accumulation of a threshold quantity of photons at the detector, a signal is sent to either disable the current to the anode or to physically block the x-ray beam. This approach suffers several drawbacks in relation to the invention of this disclosure.

a) Rotating anode sources are CW or quasi-CW devices and neither interrupt methods mentioned above are instantaneous. Thus, there will be dose accumulated while the source is being shut down or is being physically blocked. On the other hand, in the case of a laser-Compton x-ray source (LCXS) or laser-Compton gamma-ray source (LCGS) x-rays or gamma-rays are produced for each interaction of a laser pulse with an electron bunch. If the signal from the detector to divert the laser pulse is fast compared to the time interval from one laser pulse to the next and the electro-optic switch operation is fast compared to the time interval from one laser pulse to the next, then the x-ray or gamma-ray source may be turned off completely before additional exposure occurs.

b) Rotating anode devices operate with beams of electrons impinging upon the anode material at a constant rate. Interruption of the electron beam current, can change the electromagnetic environment around the anode and the thermal loading of the anode material. Re-initiation of electron beam does not necessarily instantaneously produce the same electron beam focus or x-ray flux as that occurring during steady state operation. On the other hand, in the case of the LCXS by electro-optically diverting the laser pulses from interacting with the electron beam, one does not change the electron beam dynamics of the electron beam used in a laser-Compton source. The electron beam may remain on and operational even without producing x-rays or gamma-rays if there are no laser photons. A simple change of the electro-optic switch that returns the laser photons to the laser-electron interaction region will produce a laser-Compton source that is identical to that used to image the previous pixel.

c) Rotating anode sources are not well suited to production of highly-collimated beams of x-rays or gamma-rays. They produce light in all directions and can only produce collimated beams by passage through narrow apertures that in turn greatly reduce their flux. LCXS and LCGS devices intrinsically produce narrow beams of photons. Effectively all of the LCXS may be used for single-pixel feedback imaging while only a small portion of the output from a rotating anode source may be used in this manner.

SUMMARY OF THE INVENTION

This invention represents a new method for ultralow-dose, x-ray or gamma-ray imaging based on fast, electronic control of the output of a laser-Compton x-ray source or laser-Compton gamma-ray source (LCXS or LCGS). In this method, X-ray or gamma-ray shadowgraphs are constructed one (or a few) pixel(s) at a time by monitoring the LCXS or LCGS beam energy required at each pixel at the object to achieve a threshold level of detectability at the detector. The beam energy required to reach the detection threshold is proportional to the inverse of the opacity of the object. The beam energy to reach threshold is determined simply by measuring the illumination time required by the constant power LCXS or LCGS to achieve threshold detectability at the detector. Once the threshold for detection is reached, an electronic or optical signal is sent to the LCXS/LCGS that enables a fast optical switch that in turn diverts either in space or time the laser pulses used to create Compton photons. In this way, one prevents the object from being exposed to any further Compton x-rays or gamma-rays until either the laser-Compton beam or the object are moved so that a new pixel location may be illumination. This method constructs the image of the object with the minimal possible x-ray or gamma-ray dose. An important aspect of this invention is that this method of feedback control on the x-ray or gamma-ray source does not in any way perturb the steady state operation of the laser or accelerator subsystems of the LCXS/LCGS and thus the beam available for exposure at each imaging location is identical from pixel to pixel once the electronically activated switch is disabled. Another important aspect of this imaging system is that the dynamic range of the image is not constrained by the detector dynamic range but rather by the time one is willing to dwell at any one pixel. Uses of the invention in x-ray and gamma-ray radiographic imaging include medical imaging, industrial non-destructive evaluation of objects and precision metrology.

LCXS and LCGS have output that is polychromatic but highly angle correlated. With proper design and apertures a LCXS or LCGS may produce a narrow beam of nearly mono-energetic photons (relative bandwidth of <1%). Mono-energetic beams are able to produce x-ray and gamma-ray shadowgraphs with much less dose than anode based sources because of their lack of absorbing, low-energy photons. Tunable mono-energetic beams may also be used to take images of the same pixel above and below the k-edge of specific contrast agents and in this way be used to further reduce the dose to the object.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

In this invention, a laser-Compton x-ray source (LCXS) or a laser-Compton gamma-ray (LCGS) source is used in a feedback, pixel-by-pixel imaging configuration to create high-resolution, x-ray or gamma-ray shadowgraphs of the material and density variations within an arbitrary object. The X-ray or gamma-ray shadowgraphs are constructed one (or a few) pixel(s) at a time by monitoring the number of LCXS or LCGS beam photons required at each pixel to achieve a threshold level of detectability. The beam energy required to reach the detection threshold is proportional to the inverse of the opacity of the object. The beam energy to reach threshold is determined simply by measuring the illumination time required by the constant power LCXS or LCGS to achieve threshold detectability. Once the threshold for detection is reached, a signal is sent to the LCXS/LCGS to enable a switch to rapidly (nanoseconds) divert either in space or time the laser pulses used to create Compton photons. In this way one prevents the object from being exposed to any further Compton x-rays or gamma-rays until either the laser-Compton beam or the object are moved so that a new pixel location is ready for illumination. The image of the object is constructed with the minimal possible x-ray or gamma-ray dose. An important aspect of this invention is that this method of feedback control does not in any way perturb the steady state operation of the laser or accelerator subsystems of the LCXS/LCGS and thus the beam available for exposure at each imaging location is identical from pixel to pixel once the electro-optic switch is disabled. Another important aspect of this imaging system is that the dynamic range of the image is not constrained by the detector dynamic range but rather by the time one is willing to dwell at any one pixel.

Laser Compton scattering (sometimes also referred to as inverse Compton scattering) is the process in which an energetic laser pulse is scattered off of a short duration, bunch of relativistic electrons. This process has been recognized as a convenient method for production of short duration bursts of quasi-monoenergetic, x-ray and gamma-ray radiation. In the technique, the incident laser light induces a transverse dipole motion of the electron bunch which, when observed in the rest frame of the laboratory, appears to be a forwardly-directed, Doppler-upshifted beam of radiation. The spectrum of any laser Compton source extends from DC to 4 gamma squared times the energy of the incident laser photons for head on laser-electron collisions. (Gamma is the normalized energy of the electron beam, i.e., the energy of the electron divided by the rest mass energy of the electron. Gamma=1 when the electron energy=511 keV.)

By changing the energy of the electron bunch, beams of high energy radiation ranging from ~10 keV x-rays to >20 MeV gamma-rays have been produced and used for a wide range of applications. The spectrum of the radiated Compton light is highly angle-correlated about the propagation direction of the electron beam with highest energy photons emitted only in the forward direction. With an appropriately designed aperture placed in the path of the x-ray or gamma-ray beam, one may create quasi-monoenergetic x-ray or gamma-ray pulses of light whose bandwidth (DE/E) is typically 10% or less. At Lawrence Livermore National Laboratory (LLNL), systems have been designed for generation of narrow bandwidth (bandwidth of the order 0.1%) gamma-rays that may be used to excite isotope-specific nuclear resonances. Such beams of gamma-rays may be produced through optimized design of interaction of the laser and electron and with the use of high-quality laser and electron beams whose respective spectra are less than 0.1%.

Laser-Compton x-ray sources (LCXS) and laser-Compton gamma-ray (LCGS) sources are also highly collimated especially in comparison with conventional rotating x-ray or gamma-ray bremsstrahlung sources. The cone angle for emission of the half bandwidth spectrum is approximately 1 radian on gamma or of order milliradians while the cone angle for narrowest bandwidth, on-axis spectrum may be of order 10 micro-radians. Typical rotating anode sources have beam divergences of ~500 milli-radians. It is this high degree of collimation that makes LCXS or LCGS devices ideally suited for pixel by pixel imaging modalities. For example a 0.1% bandwidth LCGS may have a beam diameter of order 100 microns even at a distance of a meter from the point of gamma-ray creation.

Figure 1:
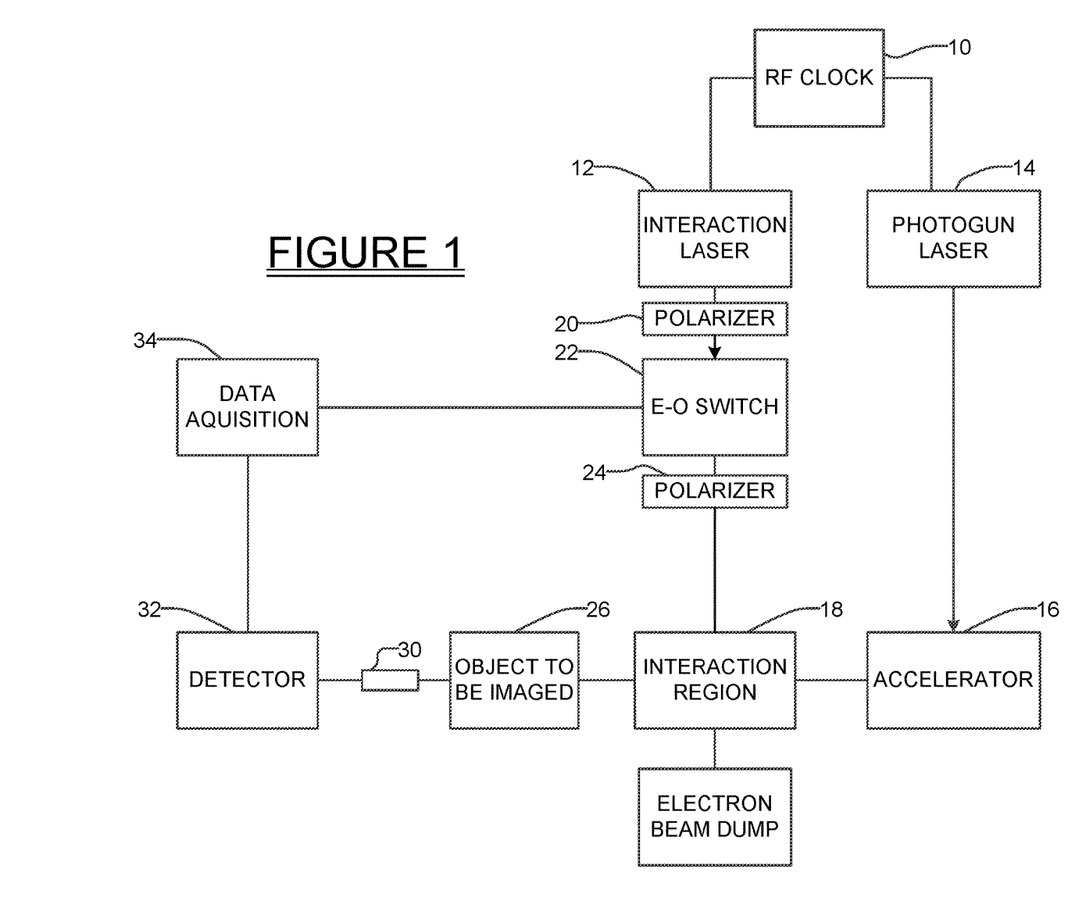
FIG. 1 shows an exemplary overall layout of an embodiment of the invention that utilizes an electro-optical switch after the laser amplifier.

The basic design of laser-Compton x-ray and laser-Compton gamma-ray sources are known in the art. See, e.g., U.S. Pat. No. 8,934,608, titled "High Flux, Narrow Bandwidth Compton Light Sources Via Extended Laser-Electron Interactions," incorporated herein by reference. For example, in U.S. Pat. No. 8,934,608, a laser system provides a UV beam to drive the photogun of the linear accelerator. In one embodiment, interruption of this laser beam will turn off the electron bunches provided from the linear accelerator. In the remaining disclosure, the output of either x-rays of gamma-rays from the laser-Compton source may be referred to as a Compton beam. FIG. 1 shows an exemplary overall layout of an embodiment of the invention that utilizes an electro-optical switch after the laser amplifier of a laser-Compton source. In the figure, an RF clock 10 synchronizes both the interaction laser 12 and the photogun laser 14. The photogun laser 14 illuminates the photo-cathode of the linear accelerator 16 which provides electron bunches to interaction region 18 as is known in the art. The output from interaction laser 12 is linearly polarized by polarizer 20 the output of which is directed to an electro-optic modulator 22. In one embodiment, if no voltage is applied to the E-O modulator 22, the laser light having the linear polarization set by polarizer 20 will be allowed to pass through polarizer 24 and propagate into interaction region 18 where it collides with the electron bunches to produce a Compton beam which is directed to an object 26 to be imaged. Based on this disclosure, those skilled in the art will recognize that a variety of means can be used in place of the combination of polarizers and E-O modulator described above for allowing or preventing the output laser beam from propagating into interaction region 18. Preventing the output laser beam from colliding with the electron bunches will effectually switch the system off and no x-rays or gamma-rays will be produced to propagate onto the object. Electrons that are scattered from the collision with the laser beam are collected in an electron beam dump 28. The system is configured so that a portion of the Compton beam that passes through the object will in turn pass through a collimation tube 30 before propagating onto detector 32. A computer system 34 having data acquisition and means for controlling the E-O switch is connected between the detector and the E-O switch. In operation, the laser beam is allowed to propagate into the interaction region such that a Compton beam is produced only for a period of time necessary for at least one pixel of the detector to register a predetermined signal threshold. Once this threshold has been met, the computer system operates the E-O modulator to prevent the laser beam from propagating any further, thereby shutting of the production of the Compton beam. The object or the Compton beam can be moved to a different location on the object and the Compton beam is then turned on again until a detection threshold is met. In this manner, an image of the object density can be produced. By allowing only the amount of radiation from the Compton beam to propagate onto each object location as is needed to achieve a threshold of detection, the amount of radiation absorbed by the object is minimized at each location on the object that the measurement is made.

As briefly discussed above, the output from a LCXS or LCGS is dependent upon the simultaneous presence of laser photons and electrons at the point of collision, which is sometimes referred to as the interaction point or, in the above example, as interaction region 18. Removal of either the laser photons or the electrons from reaching the point of collision eliminates the output of the source completely. If one wishes to rapidly turn off the x-ray or gamma-ray output there are a number of alternatives, some of which are described below. Other alternatives will be apparent to those skilled in the art based on this disclosure and as such are within the scope of this invention.

Figure 2:
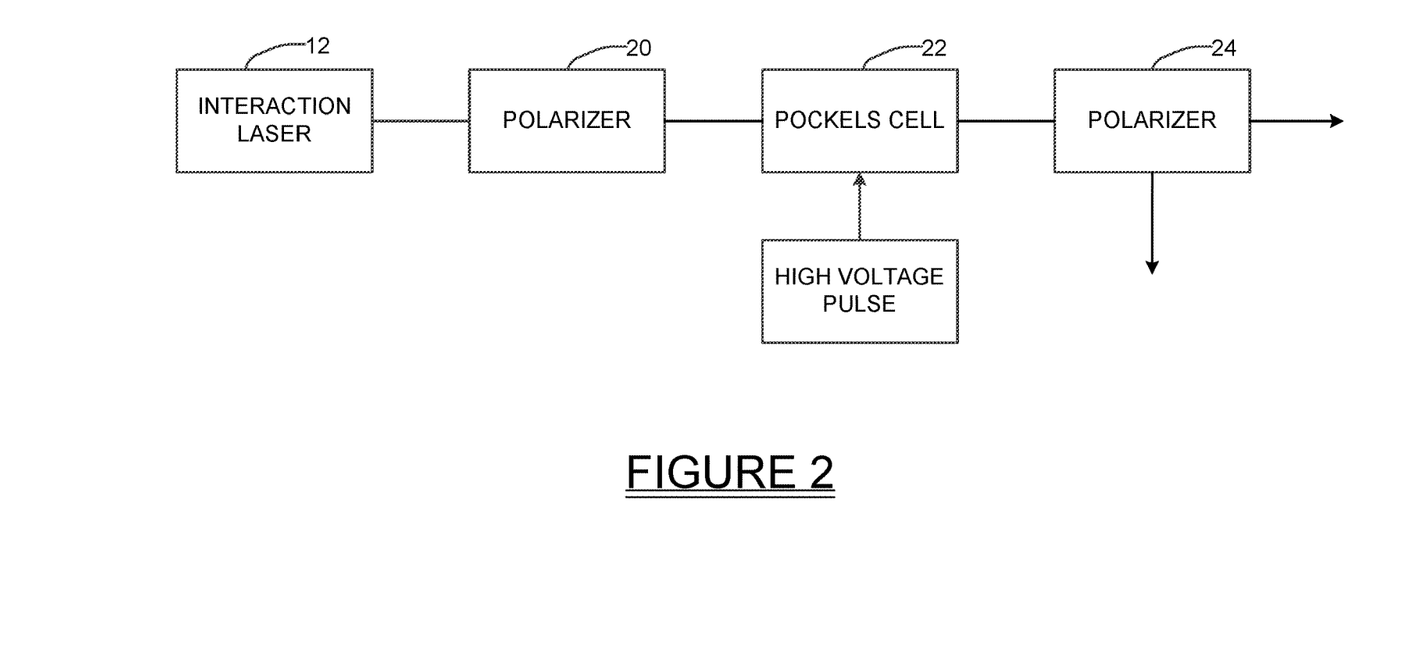
FIG. 2 shows an example of "spatial diversion" of the interaction laser output.

1) One switching method is to divert the laser pulse from the interaction region. This may be accomplished by passing a polarized laser pulse through an electro-optic switch comprised of a Pockels cell and a polarizer. An example of such configuration was described above in the embodiment of FIG. 1. FIG. 2 shows an expanded view of such a "spatial diversion" of the interaction laser 12 output described in the embodiment of FIG. 1. Voltage 34' applied to the E-O modulator (Pockels cell) 22 rotates the polarization of the laser pulse. A half wave voltage will rotate the polarization by 90 degrees and thus change the direction of the beam on the polarizer 24. The advantages of this method are that it is fast since the Pockels cell may be pulsed with nanosecond pulses, it is capable of switching energetic laser pulses (joule level and above), and the method leaves the bulk of the upstream laser system unchanged either thermally or optically. This method of course also does not perturb the electron accelerator at all. This method also has the shortest delay between the detector and an "off" state of the Compton source.

2) Another switching method is to divert the seed laser pulse prior to amplification in the laser chain. This may be done via a number of electro-optic methods including that described above but also via mach-zender switches similar to that used in the telecom industry or via acousto-optics switches. The advantages here are that the switches may be faster (sub-nanosecond) due to the smaller size of the laser beam and that the cost and size of the switching device may also be smaller. The disadvantage is that the bulk of the laser amplification chain does not remain unchanged thermally and thus there may be transient distortions on the laser beam upon re-seeding of the amplification chain. In this embodiment, the mach-zender switch is located between the seed beam and the amplifier. Mach-zender switches themselves are known in the art.

3) Still another switching method is to divert the UV laser pulse that creates the electron bunches in linear accelerator. The switching in this case can have the advantages outlined in 2) above. The disadvantage is that steady state electron accelerator performance is dependent upon the electron beam charge in the accelerator structure and there may thus be transient beam changes upon restart of the electron beam.

4) Another switching method is to mistime the UV laser pulse that creates the electron bunches in the linear accelerator. The delay required to maintain the electron beam performance but to miss the laser pulse would be one RF cycle or nominally 100 ps for a high frequency RF accelerator. Because the transit time through the region over which the electron and laser pulse interact may be much shorter than 100 ps, smaller delays can effectively shut off the x-ray or gamma-ray output but these delays will also inject electrons out of phase into the accelerator and thus potentially affect the dynamics of subsequent electron bunches.

Figure 3:
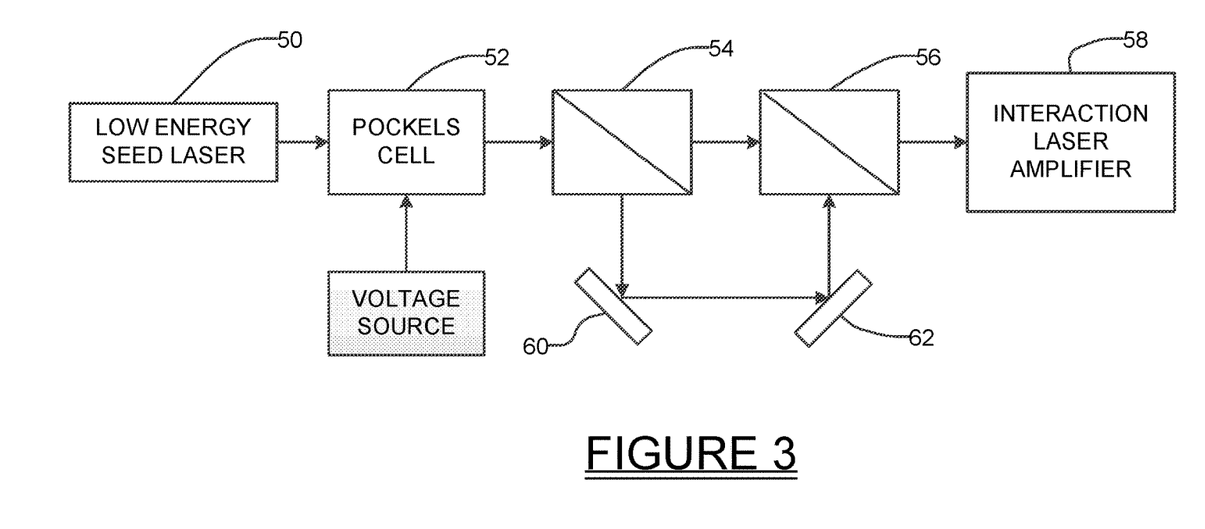
FIG. 3 illustrates an example of "temporal diversion" of the interaction laser pulse.

5) Still another switching method is to slightly mistime the seed laser pulses for the laser amplification chain. The required delay in this case is of order the transit time of the laser and electron bunch through the interaction region which is significantly smaller (picoseconds) than the gain lifetime of the laser amplifier (typically 100 s of microseconds). Such delays may be created via a number of methods electro-optically including via a Pockels cell arrangement as illustrated in FIG. 3. This method again leaves both the laser chain and the accelerator in their steady thermal and electrical configuration and thus enables an instant on and instant off mode of operation. Referring to FIG. 3, a seed beam pulse from low energy seed laser 50 propagates through a Pockels cell 52 which sets the polarization to be in parallel to the plane of the page. In this configuration, the beam passes through polarizers 54 and 56 and into the interaction laser amplifier 58. A sufficient voltage applied to the Pockels cell 52 rotates the polarization of the seed laser beam 90 degrees. This causes polarizer 54 to reflect the beam to mirror 60 which reflects the beam to mirror 62 which reflects the beam to polarizer 56 which reflects the beam into the interaction amplifier. The increased beam path distance produced by reflecting the beam by the Pockels cell causes an increased delay in the propagation time of the beam from the seed laser to the laser amplifier. As stated above, if this delay is a small fraction of the gain lifetime of the laser amplifier gain medium, the laser does not notice the change at all. In our case the change required to turn off the Compton beam is less than 1 part in 1,000,000).

Of the methods described above, 1 and 5 are preferred with 1 being preferred over 5 for Compton sources that utilize closely spaced electron bunches.

In order to accurately perform feedback imaging, the output of the source should be known by a secondary, calibrated means other than by intercepting the entire beam with an integrating detector. In the laser Compton case this can be done in a number of ways.

It is necessary to know how many photons were incident on the object in order to reach the threshold of detectability. An assumption can be made that the Compton beam has a constant output and a simple monitoring is made of the time that the beam was on before the threshold was reached. Note that this can produce erroneous results if the Compton beam changes as a function of time. The comments below get around this problem by using the unique properties of Compton beams to determine the absolute flux that illuminated the individual pixel of the object.

1) One can first measure the steady state electron beam parameters and then calibrate the x-ray or gamma-ray production as a function of the interaction laser beam energy. Since the interaction laser beam energy is not significantly attenuated by the Compton scattering process (1 part in $10^{10}$), measuring the laser pulse energy after the interaction region provides a high accuracy measurement of the laser field present during the interaction with the electron bunch which can be in turn used via the previous calibration to determine the flux of x-rays or gamma-rays produced.

2) The spectrum produced by laser-Compton scattering is highly angle correlated. For most imaging cases one will desire to use the higher-energy, near on-axis photons for feedback imaging and will remove the lower-energy (higher absorbing) off-axis photons by passing the beam through an aperture. The x-ray or gamma-ray energy deposited in this aperture is proportional to the total laser-Compton output and proportional to the on-axis flux used for the imaging. The energy deposited in the aperture may be determined in any number of ways depending upon the material composition of the aperture. If the aperture, for instance, were made of a scintillator material, one could collect the scintillation photons as a proportional measure of the total beam flux.

3) One could pass the entire beam or just the off axis portion or just the on axis portion of the beam prior to illumination of the object through a standard ionization chamber used to measure x-ray or gamma-ray dose.

After exiting the object, the un-scattered or un-attenuated transmitted beam is passed through a narrow aperture, as shown in FIG. 1, whose diameter is the size of the beam diameter. This aperture serves to reject any small-angle, scattered radiation from the illuminated object (a common issue in medical radiography). Behind the aperture is placed a highly sensitive detector whose response is optimized to be sensitive to single photons of the illuminating x-ray or gamma-rays but not to surrounding visible or UV radiation (such detectors are sometimes known as "solar blind" detectors.). Note it is not critical to have the scatter rejection aperture in front of the detector but doing so will create an image with the lowest possible dose.

The goal in x-ray or gamma-ray imaging is to determine the density variations within the object as a function of position. In this idea, such a map of density variations is obtained by illuminating one pixel (or small area of the object) at a time. The number of x-ray or gamma-ray photons incident on the object is increased from zero until a single (or few) photon(s) is detected by high-efficiency detector. The duration of the illumination and thus the number of total incident photons is recorded when this occurs and associated with the pixel. The object is then moved relative to the beam or the beam is scanned to a new location on the object and the procedure is repeated. In this way a 2D map of the number of photons required to produce a single photon or a threshold number of photons on the detector is obtained. From this, and knowledge of the overall thickness of the object as a function of 2D position, it is possible to determine the attenuation of the object as a function of 2D position and thus to construct the equivalent "radiograph" of the object that would be obtained via conventional means. Further base on this disclosure, it should be noted this procedure for creating a 2D image could be extended by those skilled in the art to produce 3D tomographic images by repeating the procedure above to produce different views of the object. Creating a 2D image in the manner described above has the following distinct advantages.

1) the total flux illuminating the object is absolutely the minimal possible to determine the attenuation at a given position. Once the threshold photon (or number of photons) has been detected at a given position, illumination is ceased and a new location is illuminated. Imagine an object in which one area that is 1/10th of the total image area has a 10× higher attenuation than the rest of the object. In conventional imaging the entire object will be subject to sufficient flux to determine the attenuation of the small dense region. If imaged by the technique described above the same information could be obtained with nominally 10× lower overall dose to the object.

2) the dynamic range of the density information obtained is not dependent upon the dynamic range of the photon detection system but rather on the dynamic range by which one can adjust the input x-ray or gamma-ray beam which in principle can be many orders of magnitude greater than that of the detector.

3) the influence of photon scattering within the object upon the image is effectively eliminated. The aperture in front of the detector, which might be a long collimated, high density tube aligned with the axis of the input beam, precludes the scattered photons from reaching the high efficiency detector.

The resolution of the image described above will be that of the beam area at the object. For laser-Compton sources optimized for collimation, the beam area at the object may be of order 100 microns. However for laser-Compton sources in which a small laser spot and small electron spot sizes are utilized to create a high flux of x-rays or gamma-rays, the x-ray or gamma-ray beam divergence may be milli-radians and the beam area at the object may be of order millimeters. However, the source size of the laser-Compton source in this case can be microns (10 microns is a readily achievable value) and thus there is potential for much higher spatial resolution imaging and indeed higher resolution than typically obtained from a rotating anode source. It is possible to use feedback imaging with a small-spot, laser-Compton configuration to achieve, low dose, high-dynamic-range, high spatial resolution images if the single pixel detector is replaced by a small area pixel array detector whose array size subtends the beam size at the object. For example if the beam size were 1 mm at the object but the source size of laser-Compton photons were 10 microns, one could use a 100×100 array of 10 micron pixels to obtain a 10 micron or better resolution images of the object. The threshold detection value that determines when to move to the next imaging location could be either determined by the total photons collected by the entire array or by the minimal level required to declare that each pixel has been sufficiently illuminated.

It should also be noted that feedback imaging with laser-Compton sources as described here, is very well suited to two-color, x-ray imaging schemes in which one exposes the object to be imaged to x-rays with energies that are both above and below the k-edge absorption of the target material. The two images are then subtracted to create a higher contrast map of the desired material than would be obtained via single color imaging. Because laser-Compton sources are highly angle correlated in their spectral output. By aperture selecting only the central portion of the laser-Compton output one may obtain a beam with bandwidth well below 10%. Slight changes in either the laser photon energy or the electron beam energy allows one to produce x-ray beams that are tuned either above or below the k-edge absorption of the desire material. The dose required to reach a threshold level of detection will of course be lower for the case of photons below the material k-edge. Deployment of feedback imaging as described here for each of the two images will thus minimize the total dose to which the object is subjected.

Finally it is important to note that while the examples presented here suggest using a Pockels cell as a fast electro-optic switch to either spatially divert the interaction laser beam from interacting with the electron beam to produce Compton photons or to temporally delay the interaction laser so that it arrives at the interaction region at a time when no electrons are present, many other electronically controlled means of spatial and temporal diversion could be envisioned. These include but are not limited to electronically triggered acousto-optic systems, electronically controlled fiber optic delay lines, direct electro-optic beam deflection, crossed laser-beam polarization rotation etc. The salient point of this invention is that the deflection or delay of the interaction laser be done in a manner that does not affect or perturb either the steady state operation of the laser or the electron beam systems of the laser-Compton source so that when the electronic signal that initiates the beam diversion or delay is removed the laser-Compton source returns immediately to its normal state of x-ray or gamma-ray production. This aspect is fundamentally different from feedback imaging performed with conventional rotating anode devices.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

I claim:
1. A method, comprising:
providing a beam from a laser Compton x-ray or gamma ray source;
directing said beam onto a first location of an object;
detecting, at a threshold of detection of a detector, a first portion of said beam that passes through said first location, to produce a first detected signal;
upon reaching said threshold of detection and producing said first detected signal, preventing said beam from propagating onto said first location;
determining a first number of photons or a first beam energy at said first location, wherein said first number of photons or said first beam energy is the amount required to produce said first detected signal at said threshold of detection;
directing said beam onto a second location of said object;
detecting, at said threshold of detection of said detector, a second portion of said beam that passes through said second location, to produce a second detected signal;
upon reaching said threshold of detection and producing said second detected signal, preventing said beam from propagating onto said second location;
determining a second number of photons or a second beam energy at said second location, wherein said second number of photons or said second beam energy is the amount required to produce said second detected signal at said threshold of detection; and
producing a map of the density of said object by spatially displaying (i) said first number of photons and said second number of photons, or (ii) said first beam energy and said second beam energy.

2. The method of claim 1, wherein said first number of photons or said first beam energy required to reach said threshold of detection is determined by measuring the illumination time required by said beam to achieve said threshold of detection.

3. The method of claim 1, wherein said beam is produced by a source that includes a linear accelerator for providing a series of bunches of relativistic electrons directed into an interaction region, wherein said source further comprises an interaction laser for providing a pulsed beam of laser light directed into said interaction region to collide with said electron bunches to produce said beam, wherein said beam is a quasi mono-energetic beam.

4. The method of claim 3, wherein the step of preventing said beam from propagating onto said first location comprises diverting in space said pulsed beam of laser light from colliding with said electron bunches.

5. The method of claim 4, wherein the step of preventing said beam from propagating onto said first location prevents said object from being exposed to said quasi mono-energetic beam any further until either said quasi mono-energetic beam or said object are moved so that a new location may be illuminated.

6. The method of claim 3, wherein the step of preventing said beam from propagating onto said second location comprises diverting in time said pulsed beam of laser light from colliding with said electron bunches.

7. The method of claim 6, wherein the step of preventing said beam from propagating onto said second location prevents said object from being exposed to said quasi mono-energetic beam any further until either said quasi mono-energetic beam or said object are moved so that a new location may be illuminated.

8. The method of claim 3, wherein the steps of preventing said beam from propagating do not in any way perturb the steady state operation of said interaction laser or said accelerator and thus the beam available for exposure at each imaging location is identical from location to location during the steps of directing said beam.

9. The method of claim 1, wherein said beam is a quasi mono-energetic beam that has a relative bandwidth of <20%.

10. The method of claim 1, wherein said beam energy to reach said threshold is determined by measuring the illumination time required by the constant power source to achieve said threshold of detectability.

11. The method of claim 3, wherein the step of preventing said beam from propagating onto said first location comprises diverting the seed laser pulse prior to amplification in the laser chain of said interaction laser.

12. The method of claim 3, wherein the step of preventing said beam from propagating onto said first location comprises diverting the UV laser pulse that creates the electron bunches in said linear accelerator.

13. The method of claim 3, wherein the step of preventing said beam from propagating onto said first location comprises mistiming the UV laser pulse that creates the electron bunches in the linear accelerator.

14. The method of claim 3, wherein the step of preventing said beam from propagating onto said first location comprises mistiming the seed laser pulses for the laser amplification chain.

15. The method of claim 14, wherein said seed laser pulses are mistimed with a delay that is of order the transit time of the laser and electron bunch through the interaction region.

16. The method of claim 3, wherein the step of determining a first number of photons or a first beam energy comprises measuring the steady state electron beam parameters and then calibrating the x-ray or gamma-ray production as a function of the interaction laser beam energy.

17. The method of claim 3, wherein the step of determining a first number of photons or a first beam energy comprises measuring the steady state electron beam parameters and then calibrating the x-ray or gamma-ray production as a function of the interaction laser beam energy, wherein the steady state electron beam parameters are measured by measuring the energy in a beam dump located after the interaction region or measuring current in a coil which is around the electron bunches.

18. The method of claim 1, wherein the step of determining a first number of photons or a first beam energy comprises passing said beam through an aperture to remove a portion of photons, wherein the x-ray or gamma-ray energy deposited in this aperture is proportional to the total laser-Compton output and proportional to the on-axis flux used for the imaging, the step comprising determining the energy deposited in said aperture.

19. The method of claim 18, wherein said aperture comprises scintillator material, wherein scintillation photons are measured and are a proportional measure of the total beam flux.

20. The method of claim 1, wherein the step of determining a first number of photons or a first beam energy comprises passing the entire beam or just the off axis portion or just the on axis portion of the beam prior to illumination of the object through a standard ionization chamber used to measure x-ray or gamma-ray dose.

21. An apparatus, comprising:
a laser Compton x-ray or gamma ray source for providing a beam, wherein said source includes a linear accelerator for providing a series of bunches of relativistic electrons directed into an interaction region, wherein said source further comprises an interaction laser for providing a pulsed beam of laser light directed to collide with said electron bunches in said interaction region to produce said beam;
a detector configured to detect a portion of said beam after it passes through a location of an object;
means for determining the number of photons or a first beam energy at said location that were required to reach a threshold level of detectability by said detector;
means for preventing said beam from propagating onto said location when said detector detects, at said threshold level of detectability, a portion of said beam that passes through said location, wherein said means for preventing said beam from propagating onto said location does not substantially affect or substantially perturb either the steady state operation of said interaction laser or said linear accelerator.

22. The apparatus of claim 21, wherein said means for determining the number of photons or a beam energy at said location measures the illumination time required by said beam to achieve said threshold level of detectability.

23. The apparatus of claim 21, wherein said means for preventing said beam from propagating diverts in space or time said pulsed beam of laser light from colliding with said electrons.

24. The apparatus of claim 21, wherein said beam is a quasi mono-energetic beam that has a relative bandwidth of <20%.

25. The apparatus of claim 21, wherein said means for preventing said beam from propagating onto said location diverts the seed laser pulse prior to amplification in the laser chain of said interaction laser.

26. The apparatus of claim 21, wherein said means for preventing said beam from propagating onto said location diverts the UV laser pulse that creates the series of bunches in said linear accelerator.

27. The apparatus of claim 21, wherein said means for preventing said beam from propagating onto said location mistimes the UV laser pulse that creates the series of bunches in said linear accelerator.

28. The apparatus of claim 21, wherein said means for preventing said beam from propagating onto said location mistimes the seed laser pulses for the laser amplification chain of said interaction laser.

29. The apparatus of claim 28, wherein said seed laser pulses are mistimed with a delay that is of order the transit time of the laser and an electron bunch through the interaction region.

30. The apparatus of claim 21, wherein said means for determining the number of photons or a beam energy at said location measures the steady state electron beam parameters of said linear accelerator and then calibrates the production of said beam as a function of the interaction laser beam energy.

31. The apparatus of claim 21, wherein said means for determining the number of photons or a beam energy at said location measures the steady state electron beam parameters and then calibrates the x-ray or gamma-ray production as a function of the interaction laser beam energy, wherein the steady state electron beam parameters are measured by measuring the energy in the beam dump after the interaction region or measuring current in a coil which is around the electron bunches.

32. The apparatus of claim 21, wherein said means for determining the number of photons or a beam energy at said location determines the energy deposited in an aperture configured to remove a portion of photons, wherein the x-ray or gamma-ray energy deposited in this aperture is proportional to the total laser-Compton output and proportional to the on-axis flux used for the imaging, the step comprising determining the energy deposited in said aperture.

33. The apparatus of claim 32, wherein said aperture comprises scintillator material, wherein scintillation photons are measured and are a proportional measure of the total beam flux.

34. The apparatus of claim 21, wherein said means for determining the number of photons or a beam energy at said location comprises an ionization chamber through which said beam passes prior to reaching said location of said object.

* * * * *